United States Patent [19]
Rao et al.

[11] Patent Number: 6,060,075
[45] Date of Patent: May 9, 2000

[54] CHECK MITE COMPOSITION AND A PROCESS FOR PREPARING THE SAME

[75] Inventors: Pillarisetti Venkata Subba Rao; Ramaswamy Sambasivam Annadurai; Malladi Srinivas, all of Bangalore, India

[73] Assignee: Vittal Mallya Scientific Research Foundation, Bangalore, India

[21] Appl. No.: 09/136,038

[22] Filed: Aug. 20, 1998

[30] Foreign Application Priority Data

Aug. 27, 1997 [IN] India ............................ 1882/MAS/97

[51] Int. Cl.[7] .................................................. A01N 25/02
[52] U.S. Cl. .................. 424/405; 424/195.1; 424/196.1; 514/461; 514/462; 514/468; 514/469; 514/470
[58] Field of Search ..................... 514/461, 462, 514/468–470; 424/405, 406, 195.1, 196.1

[56] References Cited

U.S. PATENT DOCUMENTS

| | | | |
|---|---|---|---|
| 4,666,940 | 5/1987 | Bischoff et al. | 514/544 |
| 4,806,526 | 2/1989 | Green | 514/23 |
| 5,411,992 | 5/1995 | Eini et al. | 514/731 |
| 5,472,700 | 12/1995 | Staetz et al. | 424/405 |
| 5,578,625 | 11/1996 | Suzuki et al. | |
| 5,626,848 | 5/1997 | Barnette et al. | 424/195.1 |
| 5,672,362 | 9/1997 | Burnett | |
| 5,856,526 | 1/1999 | Sankaram et al. | 549/348 |

*Primary Examiner*—Neil S. Levy
*Attorney, Agent, or Firm*—Chittaranjan N. Nirmel; Jones Jain, L.L.P.

[57] ABSTRACT

This invention relates to a composition for controlling house dust mites. The composition comprises neem seed kernel extract containing azadirachtin, an alcoholic extract of plant resins, plant polyphenols or phenolic compound, fungistat used in food industry and a dispersion medium. The invention further includes a process of preparing the same by dispersing the above ingredients in a dispersion medium.

18 Claims, No Drawings

CHECK MITE COMPOSITION AND A PROCESS FOR PREPARING THE SAME

This invention relates to a Check mite composition, and environment friendly acaricide formulation for the control of house dust mite population in the domestic environment responsible for high incidence of respiratory allergies and process of preparing the same.

BACKGROUND

The major culprits for dust allergy are mites (*Dermatophagoides farinae* and *D. pteronyssinus*) prevalent in house dust. Universally, dust mites are minute co-inhabitants in almost every household and can not be seen with the naked eye. They are found in almost all home furnishing textiles and their favourite places are mattresses, cushions, carpets, upholstery and soft toys. The reactions in hypersensitive people range from itchy and watery eyes, repeated sneezes and running nose, cough and bronchial asthma to childhood eczema. The dust on which they thrive may comprise cotton, wool lint, animal and human dander, crumbs, pollens, molds, etc.

House dust mites principally feed on human scales which are primarily found in mattresses. Bedding, carpets etc. During occupation, the temperature and humidity of the human body provides an ideal microclimate in the mattresses for dust mites. Development from egg through larva, protonymph, tritonymph to adult requires about a month in cultures, under optimum conditions. An adult mite can live up to three months. Their food comprises of protein particles and fungi present in the dust.

Mites may occasionally become airbone during bed-making. It has also been demonstrated that they secrete or release some allergens during bed-making. The allergen may comprise mites, eggs, dead mites and their excrete A gram of dust mite may contain up to 1000 mites.

Most particles of the faeces, whose physical properties are similar to pollen are deposited on the nasal mucosa and carried to the lungs causing localized inflammatory responses because of the high concentration of allergen.

Control of mite population in the domestic environment is the best method of preventing house dust allergy. The degree of cleanliness determines the number of house dust mites and the allergen level. Common control measures include vacuum cleaning, treating the carpets and bed spreads with insecticides, acaricides and fungicides. Reducing the mite population by interfering with the food chain has also been practised. However, a safe, environment friendly and effective formulation based on natural products for the control of house dust mite is not yet commercially available.

PRIOR ART

A few formulations are commercially available like Acardust, Acaroson, Allerbiocid etc., containing benzyl benzoate, the chief acaricide agent in these formulation is toxic at higher concentrations to humans as well a pets. As the effective concentration of benzyl benzoate used in these formulations is very high, its wide spread use as a domestic acaricide could be harmful.

In one acaricidal formulation, derivatives of phenols in combination with several natural oils have been used as the active acaricide agent in combination with an antibiotic Natamycin as a fungicide. But the wide spread use of phenolic derivatives and essential oils is not safe from physiological and odour point of view. Moreover, the fungicide as such can not destroy the mites.

Apart from this, a few chemicals like benzyl alcohol, primiphos methyl, dibutyl phthalate, gama-hexachlorocyclohexane and diethyl-m-toluamide have been reported in literature as miticides. But from the toxicology and environmental safety point of view their use is not recommended.

Accordingly, the object of this invention is to provide a mite control composition for domestic use which should have the following characteristics:

All the chemicals used should be safe from the toxicology point of view.

Should have multiple modes of action i.e., it should control the mite population, prevent the growth of fungi, reduce the existing allergen levels, act as a disinfectant as well as prevent the mites from developing resistance to these chemicals.

Should not have an offensive odour.

Further, re-establishment of house dust mites after treatment with acaricides is the common problem due to the existence of nymph and eggs. Moreover, the miticide cannot reach the deeper layers of carpets and upholstery. Accordingly, the second object of this invention is to control the mites and prevent its re-establishment by preparing the composition which can not only kill the adult mites but also be a ovicide and a larvicide.

To achieve the said objectives this invention provides a Check mite composition for the control of house dust mites comprising:

| | |
|---|---|
| plant derived acaricidal agent | 0.01–0.1 % wt./vol. |
| plant derived disinfectant agent | 0.1–3 % wt./vol. |
| plant derived protein denaturant | 0.1–2% wt./vol. |
| fungistat agent | 0.1–3% wt./vol. |
| dispersing agent (alcohol) | 99.69–91.9% wt./vol |

The plant derived acaricidal agent is neem seed kernel extract containing azadirachtin/azadirachtin A of 2–90% enrichment and preferably of 20–35% enrichment.

The neem seed kernel extract contains limonoids like nimbin, salannin, desacetylnimbin, desacetylsalannin, nimbandiol, azadirachtin-B and salannolacetate for preventing the mites from developing resistance against the active ingredient.

The plant derived disinfectant agent is an alcoholic extract of resins like stryax benzoin and the plant derived protein denaturant is plant polyphenols like tannic acid, condensed tannins, phenolic compounds like gallic acid and phloroglucinol.

The fungistat agents are fungicides used in food industry like natamycin, nipagin and the dispersing agents are ethanol, methanol and isopropyl alcohol.

The ingredients viz. plant derived acaricidal agent, plant derived disinfectant agent, plant derived protein denaturant and fungistat agent of this composition are solids which are dissolved in an alcoholic solvent (dispersing agent) to give a clear pale brown coloured solution.

This invention further relates to a process of preparing Check mite composition which comprises dispersing the following ingredients:

| | |
|---|---|
| plant derived acaricidal agent | 0.01–0.1% wt./vol. |
| plant derived disinfectant agent | 0.1–3% wt./vol. |

-continued

| | |
|---|---|
| plant derived protein denaturant | 0.1–2% wt./vol. |
| fungistat agent | 0.1–3% wt./vol. |
| in 99.69–91.9 wt/vol of dispersing agent (alcohol) | |

The plant derived acaricidal agent is neem seed kernel extract containing azadirachtin/azadirachtin A of 2–90% enrichment and preferably of 20–35% enrichment.

The neem seed kernel extract contains limonoids like nimbin, salannin, desacetylnimbin, desacetylsalannin, nimbandiol, azadirachtin-B and salannolacetate for preventing the mites from developing resistance against the active ingredient.

The plant derived disinfectant agent is an alcoholic extract of resins like stryax, benzoin and the plant derived protein denaturant is plant polyphenols like tannic acid, condensed tannins, phenolic compounds like gallic acid phloroglucinol.

The fungistat agents are fungicides used in food industry like natamycin, nipagin and the dispersing agents are ethanol, methanol, isopropyl alcohol.

The invention will now be described with reference to the following examples.

| S. No. | Ingredients | Weight/volume (%) |
|---|---|---|
| | EXAMPLE - 1 | |
| 1. | Neem seed kernel extract containing azadirachtin of 20% enrichment | 0.1 |
| 2. | Alcoholic extract of benzoin resin | 3.0 |
| 3. | Tannic acid | 1.0 |
| 4. | Nipagin | 1.0 |
| 5. | Ethanol | 94.9 |
| | EXAMPLE - 2 | |
| 1. | Neem seed kernel extract containing azadirachtin of 35% enrichment | 0.1 |
| 2. | Alcoholic extract of benzoin resin | 3.0 |
| 3. | Tannic acid | 1.0 |
| 4. | Nipagin | 1.0 |
| 5. | Ethanol | 94.9 |
| | EXAMPLE - 3 | |
| 1. | Neem seed kernel extract containing azadirachtin of 90% enrichment | 0.1 |
| 2. | Alcoholic extract of benzoin resin | 3.0 |
| 3. | Tannic acid | 1.0 |
| 4. | Nipagin | 1.0 |
| 5. | Ethanol | 94.9 |
| | EXAMPLE - 4 | |
| 1. | Neem seed kernel extract containing azadirachtin of 2% enrichment | 0.1 |
| 2. | Alcoholic extract of benzoin resin | 3.0 |
| 3. | Tannic acid | 1.0 |
| 4. | Nipagin | 1.0 |
| 5. | Ethanol | 94.9 |
| | EXAMPLE - 5 | |
| 1. | Neem seed kernel extract containing azadirachtin of 20% enrichment | 0.1 |
| 2. | Alcoholic extract of benzoin resin | 3.0 |
| 3. | Tannic acid | 1.0 |
| 4. | Nipagin | 1.0 |
| 5. | Isopropyl alcohol | 94.9 |
| | EXAMPLE - 6 | |
| 1. | Neem seed kernel extract containing azadirachtin of 35% enrichment | 0.1 |
| 2. | Alcoholic extract of benzoin resin | 3.0 |
| 3. | Tannic acid | 1.0 |
| 4. | Nipagin | 1.0 |
| 5. | Isopropyl alcohol | 94.9 |
| | EXAMPLE - 7 | |
| 1. | Neem seed kernel extract containing azadirachtin of 90% enrichment | 0.1 |
| 2. | Alcoholic extract of benzoin resin | 3.0 |
| 3. | Tannic acid | 1.0 |
| 4. | Nipagin | 1.0 |
| 5. | Isopropyl alcohol | 94.9 |
| | EXAMPLE - 8 | |
| 1. | Neem seed kernel extract containing azadirachtin of 2% enrichment | 0.1 |
| 2. | Alcoholic extract of benzoin resin | 3.0 |
| 3. | Tannic acid | 1.0 |
| 4. | Nipagin | 1.0 |
| 5. | Isopropyl alcohol | 94.9 |

Conclusion

Composition in Table 2 is very efficient in terms of speed of action and mite elimination. The total adult population is immobilized within an hour of treatment. A biweekly spray of 200 μl/100 mg of the culture is required for 8 weeks to completely eliminate the population. Reestablishment on treated areas is totally prevented after 8 weeks. After eradication a biweekly prophylactic spray can contain population build up.

We claim:

1. A check mite composition, comprising:
   (a) neem seed kernel extract containing about 2% to 90% azadirachtin in the extract as acaricidal agent: 0.01–0.1% wt/vol;
   (b) alcoholic extract of resins as plant derived disinfectant agent: 0.1–3% wt/vol;
   (c) plant poly phenol or phenolic compound as protein denaturant: 0.1–2% wt/vol;
   (d) fungistat used in food industry: 0.1–3% wt/vol; and
   (e) a dispersion agent: 99.69–91.9% wt/vol;
   wherein said neem kernel extract and the alcohol extract of resins are active ingredients.

2. The composition of claim 1, wherein the neem seed kernel extract contains about 20 to 35% of azadirachtin.

3. The composition of claim 1 wherein the neem seed kernel contains limonoids.

4. The composition of claim 3, wherein said limonoids is selected from the group consisting of nimbin, salannin, desacetylnimbin, desacetylsalannin, nimbandiol, azadirachtin-A, azadirachtin-B and salannolacetated for preventing mites from developing resistance to the active ingredients.

5. The check mite composition of claim 1, wherein the plant alcoholic extract of resin is styrax benzoin.

6. The check mite composition of claim 1, wherein the plant polyphenol is tannic acid or condensed tannins.

7. The composition of claim 1, wherein the phenolic compound is gallic acid or phloroglucinol.

8. The composition of claim 1, wherein the fungistat is natamycin or nipacin.

9. The composition of claim 1, wherein the dispersion agent is ethanol, methanol, or isopropyl alcohol.

10. A process of preparing a check mite composition for controlling house dust mites, comprising dispersing the following ingredients:
    (a) neem seed kernel extract containing about 2% to 90% azadirachtin in the extract as acaricidal agent: 0.01–0.1% wt/vol;

(b) alcoholic extract of resins as plant derived disinfectant agent: 0.1–2% wt/vol;

(c) plant poly phenol or phenolic compound as protein denaturant: 0.1–2% wt/vol; and (d) fungistat used in food industry: 0.1–3% wt/vol;

in 99.69–91.9% wt/vol of a dispersion agent, wherein said neem kernel extract and the alcoholic extract of resins are active ingredients.

11. The process of claim 10, wherein the neem seed kernel extract contains about 20 to 35% of azadirachtin.

12. The process of claim 10, wherein the neem seed kernel contains limonoids.

13. The process of claim 12, wherein said limonoids is selected from the group consisting of nimbin, salannin, desacetylnimbin, desacetylsalannin, nimbandiol, azadirachtin-A, azadirachtin-B and salannolacetate for preventing mites from developing resistance to the active ingredients.

14. The process of claim 10, wherein the plant alcoholic extract of resin is styrax benzoin.

15. The process of claim 10, wherein the plant polyphenol is tannic acid or condensed tannins.

16. The process of claim 10, wherein the phenolic compound is gallic acid or phloroglucinol.

17. The process of claim 10, wherein the fungistat is natamycin or nipagin.

18. The process of claim 10, wherein the dispersion agent is ethanol, methanol or isopropyl alcohol.

* * * * *